(12) United States Patent
Baranski et al.

(10) Patent No.: US 7,160,845 B2
(45) Date of Patent: Jan. 9, 2007

(54) DITHIOCARBAMATE DERIVATIVES USEFUL AS LUBRICANT AND FUEL ADDITIVES

(75) Inventors: John R. Baranski, Southington, CT (US); Theodore E. Nalesnik, Hopewell Junction, NY (US)

(73) Assignee: Crompton Corporation, Middlebury, CT (US)

( * ) Notice: Subject to any disclaimer, the term of this patent is extended or adjusted under 35 U.S.C. 154(b) by 512 days.

(21) Appl. No.: 10/815,579

(22) Filed: Mar. 31, 2004

(65) Prior Publication Data

US 2005/0222447 A1    Oct. 6, 2005

(51) Int. Cl.
*C10L 1/22* (2006.01)
*C10M 135/18* (2006.01)
*C07C 333/00* (2006.01)

(52) U.S. Cl. .................. 508/444; 508/551; 508/545; 508/567; 560/148; 558/235

(58) Field of Classification Search .................. 508/444
See application file for complete search history.

(56) References Cited

U.S. PATENT DOCUMENTS

| 4,758,362 | A | 7/1988 | Butke |
| 4,997,969 | A | 3/1991 | Luciani |
| 5,498,809 | A | 3/1996 | Emert et al. |
| 6,117,826 | A | 9/2000 | Baranski et al. |

*Primary Examiner*—Vasu Jagannathan
*Assistant Examiner*—Amy T. Lang
(74) *Attorney, Agent, or Firm*—Michael P. Dilworth

(57) ABSTRACT

Dithiocarbamate derivative compounds, useful as multi-functional additives for lubricating oils and fuels, are provided and are derived from a reaction product obtained from (a) a di(hydrocarbyl)thiocarbamate intermediate derived from the reaction of a dihydrocarbylamine and carbon disulfide; (b) an amide of the general formula $R^7CONH_2$ wherein $R^7$ is an alkylene group having 2 to about 30 carbon atoms; and (c) an effective amount of a carbonyl-containing compound.

42 Claims, No Drawings

DITHIOCARBAMATE DERIVATIVES USEFUL AS LUBRICANT AND FUEL ADDITIVES

BACKGROUND OF THE INVENTION

1. Technical Field

The present invention generally relates to dithiocarbamate derivatives and their use as multifunctional additives for lubricating oils and fuels.

2. Description of the Related Art

Automobile spark ignition and diesel engines have valve train systems, including valves, cams and rocker arms which present special lubrication concerns. It is extremely important that the lubricant, i.e., the engine oil, protects these parts from wear. It is also important for engine oils to suppress the production of deposits in the engines. Such deposits are produced from non-combustibles and incomplete combustion of hydrocarbon fuels (e.g., gasoline, diesel fuel oil) and by the deterioration of the engine oil employed. Accordingly, improving fuel economy is an important aspect of formulating an engine oil.

Zinc dialkyldithiophosphates (ZDDPs) have been used as antifatigue, antiwear, antioxidant, extreme pressure and friction modifying additives for lubricating oils for many years. However, they are subject to several drawbacks owing to their zinc and phosphorus contents. The presence of zinc contributes to the emission of particulates in the exhaust. In addition, during operation of an internal combustion engine, lubricating oil enters the combustion chambers by means such as clinging to cylinder walls as the piston makes its down stroke. When phosphorus-containing lubricating oil compositions enter the combustion reaction, phosphorus enters the exhaust stream where it acts as a catalyst poison thus shortening the useful life of the catalytic converter.

This is a major concern as effective catalytic converters are needed to reduce pollution and to meet governmental regulations designed to reduce toxic gases such as, for example, hydrocarbons, carbon monoxide and nitrogen oxides, in internal combustion engine exhaust emissions. Such catalytic converters generally use a combination of catalytic metals, e.g., platinum or variations, and metal oxides, and are installed in the exhaust streams, e.g., the exhaust pipes of automobiles, to convert the toxic gases to nontoxic gases. As previously mentioned, these catalyst components are poisoned by the phosphorous, or the phosphorous decomposition product of the zinc dialkyldithiophosphate; and accordingly, the use of engine oils containing phosphorous additives may substantially reduce the life and effectiveness of catalytic converters. Therefore, it would be desirable to reduce the phosphorous content in the engine oils so as to maintain the activity and extend the life of the catalytic converter.

There is also governmental and automotive industry pressure towards reducing the phosphorous content. For example, United States Military Standards MIL-L-46152E and the ILSAC Standards defined by the Japanese and United States Automobile Industry Association at present require the phosphorous content of engine oils to be at or below 0.10 wt. % with future phosphorous content being proposed to even lower levels. Accordingly, it would be desirable to replace or at least decrease the amount of zinc dialkyldithiophosphate in lubricating oils still further, thus reducing catalyst deactivation and hence increasing the life and effectiveness of catalytic converters while also meeting future industry standard proposed phosphorous contents in the engine oil.

However, simply decreasing the amount of zinc dialkyldithiophosphate presents problems because this may lower the antifatigue, antiwear, antioxidant, extreme pressure and friction modifying properties of the lubricating oil. Therefore, it is necessary to find a way to reduce the zinc and phosphorous content while still retaining antifatigue, antiwear, antioxidant, extreme pressure and friction modifying properties of the higher zinc and phosphorous content engine oils.

It would therefore be desirable to develop additives for lubricating oils that can improve the antifatigue, antiwear, antioxidant, extreme pressure and friction modifying properties of the oil while reducing the content of phosphorous of the lubricating oils.

SUMMARY OF THE INVENTION

The present invention relates to dithiocarbamate derivative compounds which are useful as ashless anti-wear, antioxidant, friction reducing, and extreme pressure additives for lubricating oils. The dithiocarbamate derivative compounds are also useful as fuel additives. Accordingly, in one embodiment of the present invention, a dithiocarbamate derivative compound is provided having the general formula:

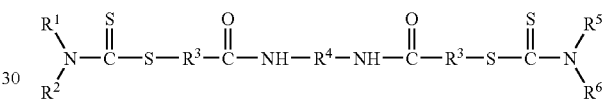

wherein $R^1$, $R^2$, $R^5$ and $R^6$ are each independently $C_1$–$C_{30}$ n-alkyl, $C_3$–$C_{30}$ branched alkyl, $C_3$–$C_{12}$ cycloalkyl, $C_5$–$C_{12}$ aryl, or $C_6$–$C_{12}$ alkylaryl; $R^3$ are each independently $C_2$–$C_{30}$ alkylene and $R^4$ is $C_1$–$C_{20}$ alkylene substituted with a compound selected from the group consisting of

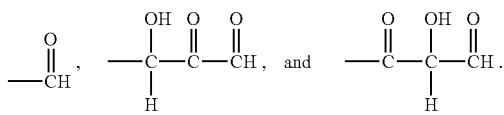

In another embodiment of the present invention, a lubricating oil composition is provided comprising (a) an oil of lubricating viscosity and (b) a functional property-improving effective amount of at least one of the foregoing dithiocarbamate derivative compound.

The present invention further relates to a method for improving at least one functional property of a lubricating oil composition which comprises adding to an oil of lubricating viscosity a functional property-improving amount of at least one of the foregoing dithiocarbamate derivative compounds.

Another embodiment provided herein is a reaction product of (a) a di(hydrocarbyl)thiocarbamate intermediate derived from a dihydrocarbylamine and carbon disulfide; (b) an amide of the general formula $R^7CONH_2$ wherein $R^7$ is an alkylene group having 2 to about 30 carbon atoms and (c) an effective amount of a carbonyl-containing compound.

Yet another embodiment of the present invention is a lubricating oil composition comprising (a) an oil of lubricating viscosity and (b) a functional property-improving effective amount of the foregoing reaction products are also provided.

Still yet another embodiment of the present invention is a fuel composition comprising (a) a major amount of a hydrocarbon fuel and (b) a minor effective amount of the foregoing reaction products.

DETAILED DESCRIPTION OF THE PREFERRED EMBODIMENTS

Generally, the dithiocarbamate derivative compounds of the present invention can be obtained from a reaction product of (a) a di(hydrocarbyl)thiocarbamate intermediate; (b) an amide of the general formula $R^7CONH_2$ wherein $R^7$ is an alkylene group having 2 to about 30 carbon atoms and (c) an effective amount of a carbonyl-containing compound. The reaction is advantageously conducted in the substantial absence of an acid neutralization agent, e.g., sodium hydroxide. Following the reaction, the compounds therein can be separated by conventional techniques, e.g., column chromatography.

In general, the di(hydrocarbyl)thiocarbamate intermediate is prepared by first reacting a dihydrocarbylamine with an equimolar to slight molar excess of carbon disulfide to provide a di(hydrocarbyl)thiocarbamate intermediate. Useful dihydrocarbylamines are those in which hydrocarbyl groups are selected from among alkyl, cycloalkyl, alkaryl and aralkyl groups of 1 to about 60 carbon atoms. Preferred dihydrocarbylamine reactants are dialkylamines in which each alkyl group contains from about 2 to about 30, and more preferably from about 4 to about 24, carbon atoms.

Next, the foregoing di(hydrocarbyl)thiocarbamate intermediate is reacted with an equimolar amount of an amide of the general formula $R^7CONH_2$ wherein $R^7$ is an alkylene group having 2 to about 30 carbon atoms and preferably from 2 to about 12 carbon atoms to form a di(hydrocarbyl) thiocarbamyl amide intermediate. Preferably, the amide compound is acrylamide. The di(hydrocarbyl)thiocarbamyl amide intermediate is reacted with a carbonyl containing compound such as, for example, a dialdehyde, e.g., glyoxal, glutaraldehyde, and the like with glyoxal being preferred, to provide the dithiocabamate derivative compounds of this invention. Generally, the molar effective amount of the carbonyl containing compound can be varied so as to obtain the desired final product composition. The effective amount utilized can vary from about 0.1 to about 3 molar equivalents.

Preferred dithiocarbamate derivative compounds of the present invention have the following general formula:

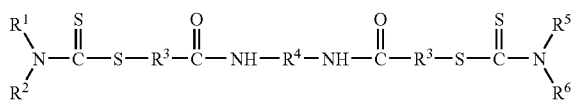

wherein $R^1$, $R^2$, $R^5$ and $R^6$ are each independently $C_1-C_{30}$ n-alkyl, $C_3-C_{30}$ branched alkyl, $C_3-C_{12}$ cycloalkyl, $C_5-C_{12}$ aryl, or $C_6-C_{12}$ alkylaryl, preferably each independently a straight-chained, branched or cyclic alkyl group of from about 2 to about 30 carbon atoms, more preferably, an alkyl group of from about 4 to about 24 carbon atoms; $R^3$ are each independently $C_2-C_{30}$ alkylene, preferably a divalent alkylene group of from about 2 to about 12 carbon atoms, more preferably a divalent alkylene group of from 2 to about 6 carbon atoms and $R^4$ is $C_1-C_{20}$ alkylene, preferably a divalent alkylene group of from 1 to about 12 carbon atoms, more preferably a divalent alkylene group of from 1 to about 6 carbon atoms and substituted with a compound selected from the group consisting of

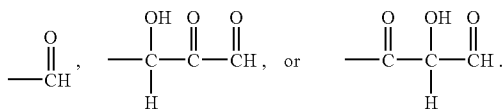

Generally, in formulating the lubricating oil composition of the present invention containing one or more of the foregoing dithiocarbamate derivative compounds, any suitable oil of lubricating viscosity may be used herein including those oils defined as American Petroleum Institute Groups I, II, and III, and can be of any suitable lubricating viscosity range, for example, having a kinematic viscosity range at 100° Centigrade (C.) of about 2 centistokes (cSt) to about 1,000 cSt, and preferably about 2 cSt to about 100 cSt at 100° C.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like, including those oils defined as American Petroleum Institute Groups I, II, and III, can be employed as the lubricant vehicle.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{18}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500–1000, diethyl ether of polypropylene glycol having a molecular weight of 1,000–1,500, etc.) or mono- and polycarboxylic esters thereof such as, for example, the acetic esters, mixed $C_3-C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl)silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The dithiocarbamate derivative compound additives of this invention are useful in lubricating oil compositions. They are multi-functional additives for lubricants and are utilized in a functional property-improving effective amount as well as an anti-wear improving effective amount, friction reducing effective amount and an antioxidant improving effective amount when added to engines operated with the oils, e.g., two-cycle engines, internal combustion engines such as, for example, gasoline (spark ignition) engines and diesel (compression ignition) engines with or without exhaust gas recirculation (EGR). The additives of the present invention can also be used in gas engines, or turbines, automatic transmission fluids, gear lubricants, metal-working lubricants, hydraulic fluids, and other lubricating oil and grease compositions. Generally, concentrations of from about 0.1 to about 10 weight percent, based on the total weight of the lubricating oil composition, can be used. Preferably, the concentration is from about 0.2 to about 2 weight percent, based on the total weight of the lubricating oil composition.

If desired, the additives of this invention can be used in combination with other additives typically found in lubricating oils and such combinations may, in fact, provide synergistic effects toward improving desired properties, such as improved deposit control, anti-wear, frictional, antioxidant, low temperature, and like properties, to the lubricating oil. Examples of additives found in lubricating oils include, but are not limited to, dispersants, detergents, rust inhibitors, antioxidants, antiwear agents, antifoaming agents, friction modifiers, seal swell agents, demulsifiers, VI improvers, pour point depressants and the like and combinations thereof. See, e.g., U.S. Pat. No. 5,498,809 for a description of useful lubricating oil composition additives. These additives are generally employed at the usual levels in accordance with well known practice.

Useful dispersants include, but are not limited to, polyisobutylene succinimides, polyisobutylene succinate esters, Mannich Base ashless dispersants, and the like. Useful detergents include, but are not limited to, metallic alkyl phenates, sulfurized metallic alkyl phenates, metallic alkyl sulfonates, metallic alkyl salicylates, and the like. Useful antioxidant additives for use in combination with the additives of the present invention include, but are not limited to, alkylated diphenylamines, N-alkylated phenylendiamines, hindered phenolics, alkylated hydroquinones, hydroxylated thiodiphenyl ethers, alkylidenebisphenols, oil soluble copper compounds, and the like. Useful anti-wear additives for use in combination with the additives of the present invention include, but are not limited to, organo borates, organo phosphites, organic sulfur-containing compounds, zinc dialkyl dithiophosphates, zinc diaryl dithiophosphates, phosphosulfurized hydrocarbons, and the like. Useful friction modifiers for use in combination with the additives of the present invention include, but are not limited to, fatty acid esters and amides, organo molybdenum compounds, molybdenum dialkylthiocarbamates, molybdenum dialkyl dithiophosphates, and the like. Useful antifoaming agents include, but are not limited to, polysiloxane, and the like. An example of a rust inhibitor is polyoxyalkylene polyols, and the like. Useful VI improvers include, but are not limited to, olefin copolymers and dispersant olefin copolymers, and the like. An example of a pour point depressant is polymethacrylate, and the like.

Lubricating oil concentrates are also contemplated herein. These concentrates usually include at least from about 90 wt. % to about 10 wt. % and preferably from about 90 wt. % to about 50 wt. %, of an oil of lubricating viscosity and from about 10 wt. % to about 90 wt. %, and preferably from about 10 wt. % to about 50 wt. %, of the additives of the present invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions.

The dithiocarbamate derivative compound additives of this invention are also useful in fuel compositions. Suitable fuels include any internal combustion engine hydrocarbon fuel, e.g., diesel, gasoline, kerosene, jet fuels, etc.; alcoholic fuels such as methanol or ethanol; or a mixture of any of the foregoing. When the fuel is diesel, such fuel generally boils above about 212° F. The diesel fuel can comprise atmospheric distillate or vacuum distillate, or a blend in any proportion of straight run and thermally and/or catalytically cracked distillates.

When the fuel is gasoline, it can be derived from straight-chain naphtha, polymer gasoline, natural gasoline, catalytically cracked or thermally cracked hydrocarbons, catalytically reformed stocks, etc. It will be understood by one skilled in the art that gasoline fuels typically boil in the range of about 80° to about 450° F. and can contain straight chain or branched chain paraffins, cycloparaffins, olefins, aromatic hydrocarbons, and any mixture of these.

Generally, the composition of the fuel is not critical and any fuel can be employed in the practice of this invention.

The concentration of the foregoing dithiocarbamate derivative compound additives of the present invention in the fuel composition can vary widely depending upon a variety of factors including, for example, the type of fuel used, the presence of other additives, etc. Generally, the concentration will range from about 10 to about 10,000 parts per million and preferably from about 30 to about 5000 parts per million of the additive per part of fuel.

The following non-limiting examples are illustrative of the present invention.

EXAMPLE 1

Preparation of di(2-ethylhexyl)dithiocarbamyl Propionamide (Amide Intermediate) (Compound 1)

To a 1-L round bottom flask equipped with an overhead stirrer and a thermocouple was added 280.0 grams (1.16 mol) of di(2-ethylhexyl)amine. 74 mL (1.22 mol) of carbon disulfide was then slowly added over 45 minutes while maintaining a temperature of 30° C. with cooling. The product was post-reacted at 30° C. for 1 hour. Next, 164.8 grams of a 50-weight percent aqueous acrylamide solution (1.16 mol) was added over a 15-minute period and then heated to 80° C. over a 45-minute period. The product was post-reacted at 80° C. for 3 hours. The reactants were cooled to 50° C. and transferred to a 1-L separatory funnel. 300 mL reagent heptanes was added to facilitate separation. The organic layer was transferred to a 1-L flask and volatiles were removed by vacuum distillation. 439.6 grams of a medium yellow, moderate viscosity liquid was recovered.

EXAMPLE 2

Preparation of Product 1

To a 1-L round bottom flask equipped with an overhead stirrer and a thermocouple was added 280.0 grams (1.16 mol) of di(2-ethylhexyl)amine. 74 mL (1.22 mol) of carbon disulfide was slowly added over 45 minutes while maintaining a temperature of 30° C. with cooling. The product was post-reacted at 30° C. for 1 hour. Next, 164.8 grams of a 50-weight percent aqueous acrylamide solution (1.16 mol) was added over a 15-minute period and then heated to 75° C. over a 45-minute period. The product was post-reacted at 75° C. for 2.5 hours. Next, 105.1 grams of 40-wt % glyoxal solution (0.72 mol) was added and reacted at 75° C. for 7 hours. The volatiles were then removed by vacuum distillation at 75° C., 29.1 in Hg for 1.5 hours and 476 grams of a dark brown, viscous liquid product was recovered. HPLC analysis of Product 1 showed 37.16 relative area percent compound 1, 5.10 relative area percent compound 2, 22.80 relative area percent compound 3, 4.54 relative area percent compound 4. Compounds 1–4 are set forth below:

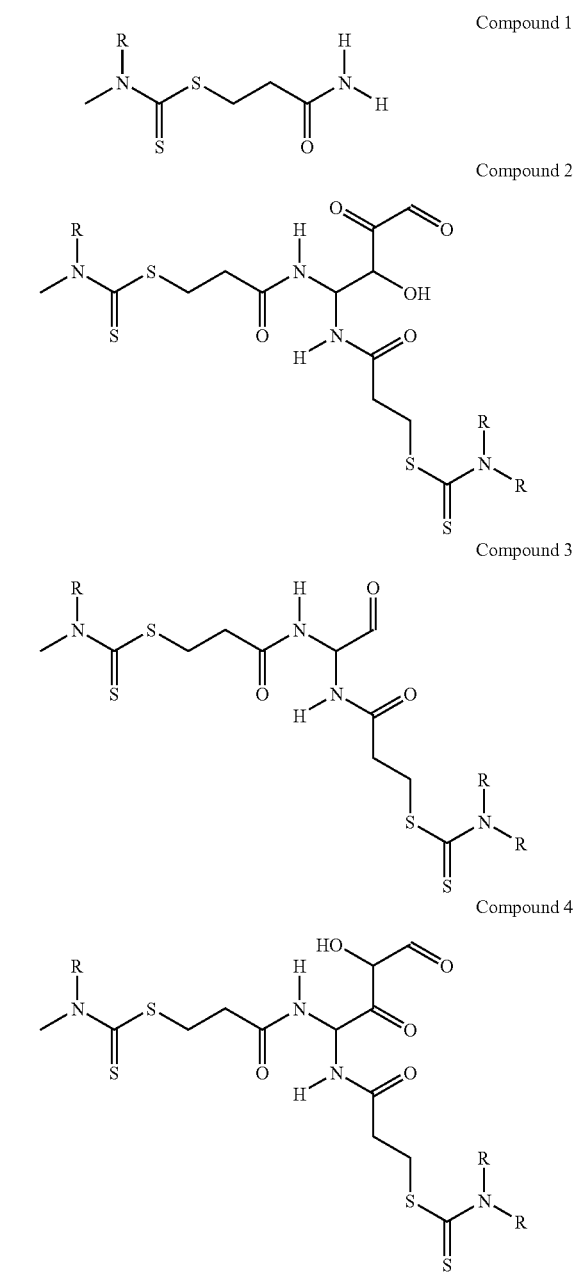

wherein R is 2-ethylhexyl.

EXAMPLE 3

Preparation of Product 2

To a 1-L round bottom flask equipped with an overhead stirrer and a thermocouple was added 280.0 grams (1.16 mol) of di(2-ethylhexyl)amine. 74 mL (1.22 mol) of carbon disulfide was slowly added over 45 minutes while maintaining a temperature of 30° C. with cooling. The product was post-reacted at 30° C. for 1 hour. 164.8 grams of a 50-weight percent aqueous acrylamide solution (1.16 mol) was added over a 15-minute period and then heated to 80° C. over a 45-minute period. The product was then post-reacted at 80° C. for 2.5 hours. Next, 105.1 grams of 40-wt % glyoxal solution (0.72 mol) was added and reacted at 80° C. for 3 hours. The volatiles were removed by vacuum distillation at a temperature of about 75 to 80° C., 29.4 in Hg for 1.5 hours and 474 grams of a dark brown, viscous liquid product was recovered. HPLC analysis of Product 2 showed 35.76 relative area percent compound 1, 7.21 relative area percent compound 2, 23.43 relative area percent compound 3, 4.84 relative area percent compound 4, each of compounds 1–4 being shown above.

EXAMPLE 4

Preparation of Product 3

To a 1-L round bottom flask equipped with an overhead stirrer and a thermocouple was added 280.0 grams (1.16 mol) of di(2-ethylhexyl)amine. 74 mL (1.22 mol) of carbon disulfide was slowly added over 45 minutes while maintaining a temperature of 30° C. with cooling. The product was post-reacted at 30° C. for 1 hour. 164.8 grams of a 50-weight percent aqueous acrylamide solution (1.16 mol) was added over a 15-minute period and heated to 80° C. over a 45-minute period. The product was post-reacted at 80° C. for 2.5 hours. Next, 105.1 grams of 40-wt % glyoxal solution (0.72 mol) was added and reacted at 90° C. for 7 hours. The volatiles were removed by vacuum distillation at a temperature of about 75 to 80° C., 29.4 in Hg for 1.5 hours and 470 grams of a dark brown, viscous liquid product was recovered. HPLC analysis of Product 3 showed 42.46 relative area percent compound 1, 5.63 relative area percent compound 2, 24.71 relative area percent compound 3, 4.52 relative area percent compound 4, each of compounds 1–4 being shown above.

EXAMPLE 5

Preparation of Product 4

To a 1-L round bottom flask equipped with an overhead stirrer and a thermocouple was added 280.0 grams (1.16 mol) of di(2-ethylhexyl)amine. 74 mL (1.22 mol) of carbon disulfide was slowly added over 45 minutes while maintaining a temperature of 30° C. with cooling. The product was post-reacted at 30° C. for 1 hour. 164.8 grams of a 50-weight percent aqueous acrylamide solution (1.16 mol) was added over a 15-minute period and heated to 80° C. over a 45-minute period. The product was then post-reacted at 80° C. for 3 hours. Next, 96.7 grams of 40-wt % glyoxal solution (0.67 mol) was added and reacted at 80° C. for 5 hours. The volatiles were removed by vacuum distillation at a temperature of about 75 to 80° C., 29.4 in Hg for 1.5 hours and 471 grams of a dark brown, viscous liquid product was recovered. HPLC analysis of Product 4 showed 39.91 relative area percent compound 1, 6.46 relative area percent compound 2, 23.76 relative area percent compound 3, 5.00 relative area percent compound 4, each of compounds 1–4 being shown above.

Four-ball Anti-wear Test

SAE 10W–30 motor oil formualations described in Table 1 below were prepared.

TABLE 1

SAE 10W-30 Motor Oil Formulations

| Ingredient | wt. % |
| --- | --- |
| Solvent Neutral 100 | 22.8 |
| Solvent Neutral 150 | 60.0 |
| Succinimide Dispersant | 7.5 |
| Overbased Calcium Phenate Detergent | 2.0 |
| Neutral Calcium Antioxidant | 0.5 |
| Rust Inhibitor | 0.1 |
| Pour Point Depressant | 0.1 |
| OCP VI Improver | 5.5 |
| Anti-wear Additive[1] | 1.0 |

[1]In the case of no anti-wear additive in Table 1, solvent neutral 150 is put in its place at 1.0 weight percent.

Compound 1 and Product 1–4 were added to the oil formulation described above in Table 1 in amounts of 0.5 wt. % and 1 wt. %, respectively, and tested in a Four-Ball Wear Test as described in ASTM D4172. The fully formulated lubricating oils tested also contained 1 wt. % cumene hydroperoxide to help simulate the environment within a running engine. The results of this testing are also included in Table 2. The additives were tested for effectiveness in two motor oil formulations (See description in Table 2). In Table 2, the numerical value of the test results (Average Wear Scar Diameter, mm) decreases with an increase in effectiveness.

| Compound (mm) | 1 wt % additive Wear Scar Diameter (mm) | 0.5 wt % additive Wear Scar Diameter (mm) |
| --- | --- | --- |
| No anti-wear additive | 0.93 | 0.93 |
| Zinc dialkyldithiophosphate | 0.46 | 0.48 |
| Compound 1 | 0.50 | 0.71 |
| Product 1 | 0.40 | 0.35 |
| Product 2 | 0.43 | 0.43 |
| Product 3 | 0.42 | 0.46 |
| Product 4 | 0.41 | 0.53 |

As the data show, Product 1–4 each show excellent antiwear performance at 1 wt % and 0.5 wt %.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A dithiocarbamate derivative compound of the general formula:

$$\begin{array}{c} R^1 \\ \phantom{R}\backslash \\ \phantom{RR}N-\overset{S}{\underset{\parallel}{C}}-S-R^3-\overset{O}{\underset{\parallel}{C}}-NH-R^4-NH-\overset{O}{\underset{\parallel}{C}}-R^3-S-\overset{S}{\underset{\parallel}{C}}-N \\ \phantom{RR}/ \phantom{NNNNNNNNNNNNNNNNNNNNNNNNNNNNNNNNN} \backslash \\ R^2 \phantom{NNNNNNNNNNNNNNNNNNNNNNNNNNNNNNNNNNNN} R^6 \end{array} \begin{array}{c} R^5 \\ \\ \end{array}$$

wherein $R^1$, $R^2$, $R^5$ and $R^6$ are each independently $C_1$–$C_{30}$ n-alkyl, $C_3$–$C_{30}$ branched alkyl, $C_3$–$C_{12}$ cycloalkyl, $C_5$–$C_{12}$ aryl, or $C_6$–$C_{12}$ alkylaryl; $R^3$ are each independently $C_2$–$C_{20}$ alkylene and $R^4$ is $C_1$–$C_{20}$ alkylene substituted with a compound selected from the group consisting of $$-\overset{O}{\underset{\parallel}{C}}H, \quad -\overset{OH}{\underset{\underset{H}{|}}{C}}-\overset{O}{\underset{\parallel}{C}}-\overset{O}{\underset{\parallel}{C}}H, \text{ or } -\overset{O}{\underset{\parallel}{C}}-\overset{OH}{\underset{\underset{H}{|}}{C}}-\overset{O}{\underset{\parallel}{C}}H.$$

2. The dithiocarbamate derivative compound of claim 1, wherein $R^1$, $R^2$, $R^5$ and $R^6$ are each independently a straight-chained, branched or cyclic alkyl group of from about 2 to about 30 carbon atoms; $R^3$ is a divalent alkylene group of from about 2 to about 12 carbon atoms; and the alkylene group of $R^4$ is a divalent alkylene group of from 1 to about 12 carbon atoms.

3. The dithiocarbamate derivative compound of claim 1, wherein $R^1$, $R^2$, $R^5$ and $R^6$ are each independently a straight-chained, branched or cyclic alkyl group of from about 4 to about 24 carbon atoms; $R^3$ is a divalent alkylene group of from 2 to about 6 carbon atoms; and the alkylene group of $R^4$ is a divalent alkylene group of from 1 to about 6 carbon atoms.

4. The dithiocarbamate derivative compound of claim 2, wherein the alkylene group of $R^4$ is substituted with $$-\overset{O}{\underset{\parallel}{C}}H.$$

5. The dithiocarbamate derivative compound of claim 3, wherein the alkylene group of $R^4$ is substituted with $$-\overset{O}{\underset{\parallel}{C}}H.$$

6. The dithiocarbamate derivative compound of claim 2, wherein the alkylene group of $R^4$ is substituted with $$-\overset{OH}{\underset{\underset{H}{|}}{C}}-\overset{O}{\underset{\parallel}{C}}-\overset{O}{\underset{\parallel}{C}}H.$$

7. The dithiocarbamate derivative compound of claim 3, wherein the alkylene group of $R^4$ is substituted with $$-\overset{OH}{\underset{\underset{H}{|}}{C}}-\overset{O}{\underset{\parallel}{C}}-\overset{O}{\underset{\parallel}{C}}H.$$

8. The dithiocarbamate derivative compound of claim 2, wherein the alkylene group of $R^4$ is substituted with $$-\overset{O}{\underset{\parallel}{C}}-\overset{OH}{\underset{\underset{H}{|}}{C}}-\overset{O}{\underset{\parallel}{C}}H.$$

9. The dithiocarbamate derivative compound of claim 3, wherein the alkylene group of $R^4$ is substituted with $$-\overset{O}{\underset{\parallel}{C}}-\overset{OH}{\underset{\underset{H}{|}}{C}}-\overset{O}{\underset{\parallel}{C}}H.$$

10. A lubricating oil composition comprising (a) an oil of lubricating viscosity and (b) a functional property-improving effective amount of at least one dithiocarbamate derivative compound of claim 1.

11. A lubricating oil composition comprising (a) an oil of lubricating viscosity and (b) an antiwear-improving effective amount of at least one dithiocarbamate derivative compound of claim 1.

12. A lubricating oil composition comprising (a) an oil of lubricating viscosity and (b) a friction reducing effective amount of at least one dithiocarbamate derivative compound of claim 1.

13. A lubricating oil composition comprising (a) an oil of lubricating viscosity and (b) an antioxidant-improving effective amount of at least one dithiocarbamate derivative compound of claim 1.

14. A method for improving at least one functional property of a lubricating oil which comprises adding to the lubricating oil a functional property-improving effective amount of at least one dithiocarbamate derivative compound of claim 1.

15. A method for improving the anti-wear property of a lubricating oil which comprises adding to the lubricating oil an anti-wear-improving effective amount of at least one dithiocarbamate derivative compound of claim 1.

16. A method for improving the friction reducing property of a lubricating oil which comprises adding to the lubricating oil a friction reducing effective amount of at least one dithiocarbamate derivative compound of claim 1.

17. A method for improving the antioxidant property of a lubricating oil which comprises adding to the lubricating oil an antioxidant-improving effective amount of at least one dithiocarbamate derivative compound of claim 1.

18. A reaction product obtained from (a) a di(hydrocarbyl) thiocarbamate intermediate derived from the reaction of a dihydrocarbylamine and carbon disulfide; (b) an amide of the general formula $R^7CONH_2$ wherein $R^7$ is an alkylene group having 2 to about 30 carbon atoms; and (c) an effective amount of a carbonyl-containing compound.

19. The reaction product of claim 18 wherein the amide is acrylamide and the carbonyl-containing compound is a dialdehyde.

20. The reaction product of claim 19 wherein the dialdehyde is selected from the group consisting of glyoxal and glutaraldehyde.

21. The reaction product of claim 18 wherein the amide is acrylamide and the carbonyl-containing compound is glyoxal.

22. The reaction product of claim 18 wherein the dihydrocarbylamine is a dialkylamine in which each alkyl group contains from about 2 to about 30 carbon atoms.

23. A lubricating oil compositions comprising (a) an oil of lubricating viscosity and (b) a functional property-improving effective amount of the reaction product of claim 18.

24. A lubricating oil compositions comprising (a) an oil of lubricating viscosity and (b) a functional property-improving effective amount of the reaction product of claim 19.

25. A lubricating oil compositions comprising (a) an oil of lubricating viscosity and (b) a functional property-improving effective amount of the reaction product of claim 21.

26. A lubricating oil composition comprising (a) an oil of lubricating viscosity and (b) an antiwear-improving effective amount of the reaction product claim 18.

27. A lubricating oil composition comprising (a) an oil of lubricating viscosity and (b) a friction reducing effective amount of the reaction product claim 18.

28. A lubricating oil composition comprising (a) an oil of lubricating viscosity and (b) an antioxidant-improving effective amount of the reaction product claim 18.

29. A method for improving at least one functional property of a lubricating oil which comprises adding to the lubricating oil a functional property-improving amount of the reaction product claim 18.

30. A method for improving the anti-wear property of a lubricating oil which comprises adding to the lubricating oil an anti-wear-improving amount of the reaction product claim 18.

31. A method for improving the friction reducing property of a lubricating oil which comprises adding to the lubricating oil a friction reducing amount of the reaction product claim 18.

32. A method for improving the antioxidant property of a lubricating oil which comprises adding to the lubricating oil an antioxidant-improving amount of the reaction product claim 18.

33. A fuel composition comprising a major amount of a hydrocarbon fuel and a minor effective amount of the dithiocarbamate derivative compound of claim 1.

34. A fuel composition comprising a major amount of a hydrocarbon fuel and a minor effective amount of the dithiocarbamate derivative compound of claim 3.

35. A fuel composition comprising a major amount of a hydrocarbon fuel and a minor effective amount of the reaction product of claim 18.

36. A fuel composition comprising a major amount of a hydrocarbon fuel and a minor effective amount of the reaction product of claim 19.

37. A fuel composition comprising a major amount of a hydrocarbon fuel and a minor effective amount of the reaction product of claim 21.

38. The fuel composition of claim 33 wherein the hydrocarbon fuel is gasoline or diesel fuel.

39. The fuel composition of claim 34 wherein the hydrocarbon fuel is gasoline or diesel fuel.

40. The fuel composition of claim 35 wherein the hydrocarbon fuel is gasoline or diesel fuel.

41. The fuel composition of claim 36 wherein the hydrocarbon fuel is gasoline or diesel fuel.

42. The fuel composition of claim 37 wherein the hydrocarbon fuel is gasoline or diesel fuel.

* * * * *